(12) United States Patent
Sprain et al.

(10) Patent No.: US 8,326,425 B2
(45) Date of Patent: Dec. 4, 2012

(54) FEEDTHROUGH CONNECTOR FOR IMPLANTABLE DEVICE

(75) Inventors: Jason W. Sprain, Shoreview, MN (US); Anthony Joseph Angelo, Forest Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 844 days.

(21) Appl. No.: 11/278,047

(22) Filed: Mar. 30, 2006

(65) Prior Publication Data
US 2007/0239222 A1    Oct. 11, 2007

(51) Int. Cl.
*A61N 1/00* (2006.01)
*H01R 13/627* (2006.01)

(52) U.S. Cl. ............... 607/36; 607/37; 439/357

(58) Field of Classification Search ........... 607/36, 607/37; 439/357
See application file for complete search history.

(56) References Cited

U.S. PATENT DOCUMENTS

| | | | |
|---|---|---|---|
| 4,352,951 A * | 10/1982 | Kyle ............. | 174/152 GM |
| 4,399,819 A | 8/1983 | Cowdery | |
| 5,235,742 A | 8/1993 | Szyszkowski | |
| 5,660,177 A | 8/1997 | Faupel et al. | |
| 5,679,026 A * | 10/1997 | Fain et al. ............. | 439/651 |
| 5,755,743 A * | 5/1998 | Volz et al. ............. | 607/37 |
| 5,759,197 A * | 6/1998 | Sawchuk et al. ....... | 607/36 |
| 5,782,891 A | 7/1998 | Hassler et al. | |
| 5,871,515 A * | 2/1999 | Wiklund et al. ........ | 607/36 |
| 5,942,842 A * | 8/1999 | Fogle, Jr. ............. | 313/313 |
| 5,951,595 A * | 9/1999 | Moberg et al. ......... | 607/37 |
| 6,026,325 A | 2/2000 | Weinberg et al. | |
| 6,044,302 A * | 3/2000 | Persuitti et al. ........ | 607/37 |
| 6,052,623 A * | 4/2000 | Fenner et al. .......... | 607/36 |
| 6,205,358 B1 | 3/2001 | Haeg et al. | |
| 6,414,835 B1 * | 7/2002 | Wolf et al. ............. | 361/302 |
| 6,428,368 B1 * | 8/2002 | Hawkins et al. ........ | 439/271 |
| 6,456,256 B1 | 9/2002 | Amundson et al. | |
| 6,459,935 B1 * | 10/2002 | Piersma ................ | 607/37 |
| 6,519,133 B1 * | 2/2003 | Eck et al. .............. | 361/302 |
| 6,566,978 B2 * | 5/2003 | Stevenson et al. ...... | 333/182 |
| 6,622,046 B2 | 9/2003 | Fraley et al. | |
| 6,765,780 B2 * | 7/2004 | Brendel et al. ......... | 361/302 |

(Continued)

FOREIGN PATENT DOCUMENTS
EP    0405838 A2    1/1991
(Continued)

OTHER PUBLICATIONS

"European Application Serial No. 07758308.6, Office Action mailed Jun. 12, 2012", 6 pgs.

(Continued)

*Primary Examiner* — Nicole F Lavert
(74) *Attorney, Agent, or Firm* — Schwegman Lundberg & Woessner, P.A.

(57) ABSTRACT

An implantable device includes a header, a pulse generator housing, one or more electrical connectors connected to the header, and a feedthrough assembly mounted to the pulse generator housing. The feedthrough assembly includes a non-conductive base having one or more holes therethrough, the feedthrough assembly further including one or more feedthrough pins, each feedthrough pin extending through one of the holes, each feedthrough pin including a pin body and an upper contact surface for connecting to one or more of the electrical connectors, the upper contact surface having a larger surface area than a cross-sectional area of the pin body.

20 Claims, 5 Drawing Sheets

U.S. PATENT DOCUMENTS

| | | | |
|---|---|---|---|
| 6,817,905 B2 | 11/2004 | Zart et al. | |
| 6,882,248 B2* | 4/2005 | Stevenson et al. | 333/182 |
| 7,035,077 B2 | 4/2006 | Brendel | |
| 7,108,711 B2* | 9/2006 | Vogel et al. | 607/1 |
| 7,274,963 B2* | 9/2007 | Spadgenske | 607/36 |
| 7,803,014 B2 | 9/2010 | Sprain et al. | |
| 2002/0027484 A1* | 3/2002 | Stevenson et al. | 333/182 |
| 2003/0040780 A1* | 2/2003 | Haeg et al. | 607/36 |
| 2003/0139096 A1* | 7/2003 | Stevenson et al. | 439/620 |
| 2004/0012462 A1* | 1/2004 | Kim | 333/182 |
| 2004/0078062 A1* | 4/2004 | Spadgenske | 607/37 |
| 2004/0116976 A1* | 6/2004 | Spadgenske | 607/37 |
| 2004/0215280 A1* | 10/2004 | Dublin et al. | 607/36 |
| 2004/0215281 A1* | 10/2004 | O'Phelan et al. | 607/36 |
| 2005/0060003 A1* | 3/2005 | Taylor et al. | 607/36 |
| 2005/0118887 A1 | 6/2005 | Hoffer et al. | |
| 2005/0247475 A1* | 11/2005 | Stevenson et al. | 174/50.51 |
| 2006/0282126 A1 | 12/2006 | Fischbach et al. | |
| 2007/0202728 A1* | 8/2007 | Olson et al. | 439/248 |
| 2007/0232119 A1 | 10/2007 | Sprain et al. | |

FOREIGN PATENT DOCUMENTS

| | | | |
|---|---|---|---|
| EP | 0916364 A2 | | 5/1999 |
| GB | 2127629 A | * | 4/1984 |
| WO | WO-03/073450 A1 | | 9/2003 |
| WO | WO-2004/105572 A2 | | 12/2004 |
| WO | WO-2007/114993 A2 | | 10/2007 |
| WO | WO-2007/117812 A2 | | 10/2007 |
| WO | WO-2007114993 A3 | | 10/2007 |
| WO | WO-2007117812 A3 | | 10/2007 |

OTHER PUBLICATIONS

"Japanese Application Serial No. 2009-503127, Examiners Decision of Final Refusal mailed May 29, 2012", With English Translation, 4 pgs.

"European Application Serial No. 07758308.6, Examination Notification Art. 94(3) mailed May 23, 2011", 7 pgs.

"European Application Serial No. 07758308.6, Examination Notification Art. 94(3) mailed Oct. 17, 2011", 5 pgs.

"European Application Serial No. 07758308.6, Examination Notification Art. 94(3) response filed Sep. 19, 2011", 7 pgs.

"Japanese Application Serial No. 2009-503127, Office Action mailed Dec. 6, 2011", 2 pgs.

"European Application Serial No. 07758308.6, Response filed Feb. 23, 2012 to Office Action mailed Oct. 17, 2011", 7 pgs.

"U.S. Appl. No. 11/278,051, Final Office Action mailed Sep. 18, 2009", 9 pgs.

"U.S. Appl. No. 11/278,051, Non Final Office Action mailed on Mar. 5, 2009", 8 pgs.

"U.S. Appl. No. 11/278,051, Non-Final Office Action mailed Feb. 9, 2010", 9 pgs.

"U.S. Appl. No. 11/278,051, Non-Final Office Action mailed Oct. 1, 2008", 8 pgs.

"U.S. Appl. No. 11/278,051, Response filed Feb. 2, 2009 to Non Final Office Action mailed Oct. 1, 2008", 9 pgs.

"U.S. Appl. No. 11/278,051, Response filed Jun. 4, 2009 to Non Final Office Action mailed Mar. 5, 2009", 8 pgs.

"U.S. Appl. No. 11/278,051, Response filed Dec. 10, 2009 to Final Office Action mailed Sep. 22, 2009", 9 pgs.

"Japanese Application Serial No. 2009-503127, Response filed Mar. 28, 2012 to Office Action mailed Dec. 6, 2011", (w/ English Translation of Amended Claims), 12 pgs.

"U.S. Appl. No. 11/278,051, Notice of Allowance mailed May 25, 2010", 6 pgs.

"U.S. Appl. No. 11/278,051, Response filed May 10, 2010 to Non Final Office Action mailed Feb. 9, 2010", 9 pgs.

"U.S. Appl. No. 11/278,051, Non-Final Office Action mailed Feb. 26, 2007", 6 pgs.

"U.S. Appl. No. 11/278,051, Response filed Nov. 5, 2007 to Non-Final Office Action mailed Aug. 3, 2007", 7 pgs.

"U.S. Appl. No. 11/278,051, Response filed May 29, 2007 to Non-Final Office Action mailed Feb. 26, 2007", 8 pgs.

"U.S. Appl. No. 11/278,051, Non-Final Office Action Mailed Aug. 3, 2007", 6 pgs.

"PCT Application No. PCT/US2007/063749, International Search Report mailed Sep. 27, 2007", 4 pgs.

"PCT Application No. PCT/US2007/063749, Written Opinion mailed Sep. 27, 2007", 7 pgs.

"PCT Application No. PCT/US2007/063897, International Search Report mailed Oct. 17, 2007", 4 pgs.

"PCT Application No. PCT/US2007/063897, Written Opinion mailed Oct. 17, 2007", 6 pgs.

"U.S. Appl. No. 11/278,051, Response filed Jun. 26, 2008 to Final Office Action mailed Jan. 29, 2008", 8 pgs.

"U.S. Appl. No. 11/278,051 Final Office Action mailed Jan. 29, 2008", 10 pgs.

* cited by examiner ical devices and more specifically to a feedthrough connector for an implantable device.

FIELD OF INVENTION

This invention relates to the field of implantable devices and more specifically to a feedthrough connector for an implantable device.

BACKGROUND

Implantable medical devices are used to treat many conditions. Implantable devices such as pacemakers and defibrillators include electronics mounted within a housing which are typically operatively connected to a lead which is implanted on or in the heart. The leads implanted in or about the heart can be used to reverse certain life threatening arrhythmia, or to stimulate contraction of the heart. Electrical energy is applied to the heart via electrodes on the leads to return the heart to normal rhythm.

An implantable device can include a pulse generator which includes a device housing electrically and mechanically connected to a header. The header is used to couple a conductor of a lead with the electronics of the implantable device. For instance, a connector assembly in the header is used to couple a cardiac stimulator system such as a pacemaker, an anti-tachycardia device, a cardiac heart failure device, a cardioverter or a defibrillator with a lead having an electrode for making contact with a portion of the heart. The header is electrically connected to the device housing by interconnects leading from the header to electrical feedthroughs which pass through the housing to connect to electronic components in the housing. There is a need for less complex manufacturing and more mechanically and electrically robust connections between the housing and the header.

SUMMARY

In one example, an implantable device includes a header, a housing, one or more electrical connectors connected to the header, and a feedthrough assembly mounted to the housing. The feedthrough assembly includes a nonconductive base having one or more holes therethrough. The feedthrough assembly further includes one or more feedthrough pins, each feedthrough pin extending through one of the one or more holes, each feedthrough pin including a pin body and an upper contact surface for connecting to one or more of the electrical connectors. The upper contact surface includes a larger surface area than a cross-sectional area of the pin body.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Figure 1:
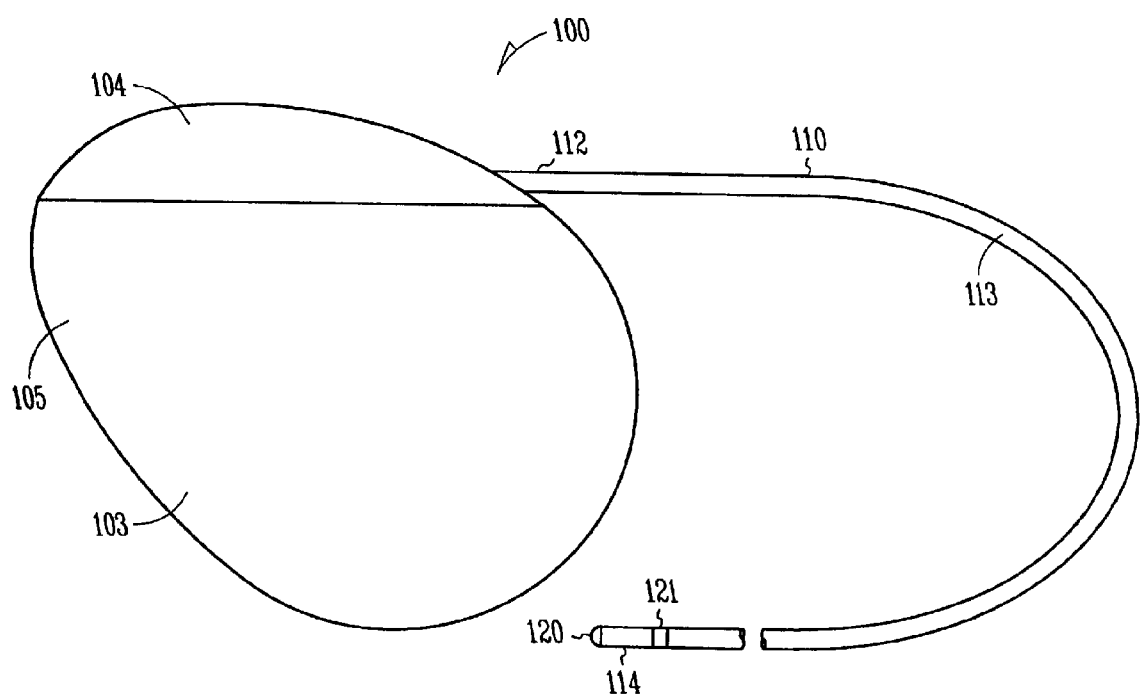
FIG. 1 shows a view of an implantable system according to at least one embodiment.

FIG. 1 shows an implantable medical device 100, in accordance with one embodiment. Device 100 includes a pulse generator 105 and at least one lead 110. The pulse generator 105 is generally implanted into a subcutaneous pocket made in the wall of the chest. Alternatively, the pulse generator 105 is placed in a subcutaneous or submuscular pocket made in the abdomen, or in other locations. Pulse generator 105 generally includes a hermetically sealed housing 103 and a header 104. Header 104 is mechanically and electrically coupled to housing 103. Pulse generator 105 can include a power supply such as a battery, a capacitor, and other components housed in housing 103. The pulse generator 105 can also include microprocessors to provide processing, evaluation, and to determine and deliver electrical shocks and pulses of different energy levels and timing for defibrillation, cardioversion, and pacing to a heart in response to cardiac arrhythmia including fibrillation, tachycardia, heart failure, and bradycardia.

Lead 110 includes a lead body 113 having a proximal end 112, where the lead is coupled at header 104 of pulse generator 105. The lead 110 extends to a distal end 114, which is coupled with a portion of a heart, when implanted. In one embodiment, the distal end 114 of the lead 110 includes one or more electrodes 120, 121 which electrically couple the lead 110 with a heart. In other examples, electrodes can be located medially or at other locations along the lead. At least one electrical conductor is disposed within the lead 110 and extends from the proximal end 112 to the electrode(s) 120, 121. The electrical conductors carry electrical current and pulses between the pulse generator 105 and the electrode(s) 120, 121.

In other embodiments, device 100 is suitable for use with implantable electrical stimulators, such as, but not limited to, pulse generators, neuro-stimulators, skeletal stimulators, central nervous system stimulators, or stimulators for the treatment of pain. The system can also be utilized as a sensor or a receiver. The electrodes can be used, for sensing, pacing, and/or shocking, for example.

Figure 2:
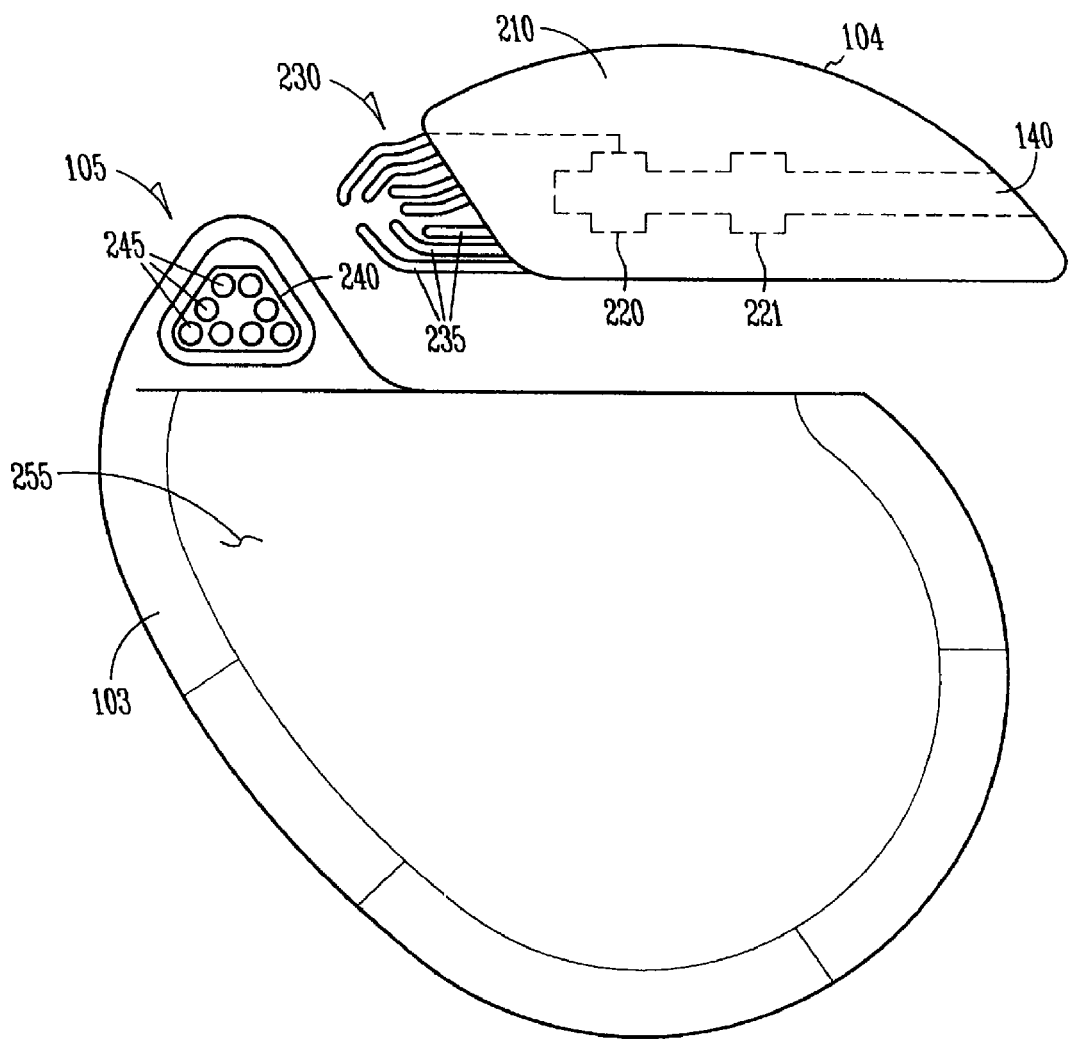
FIG. 2 shows an exploded view of the implantable device of FIG. 1.
Figure 3:
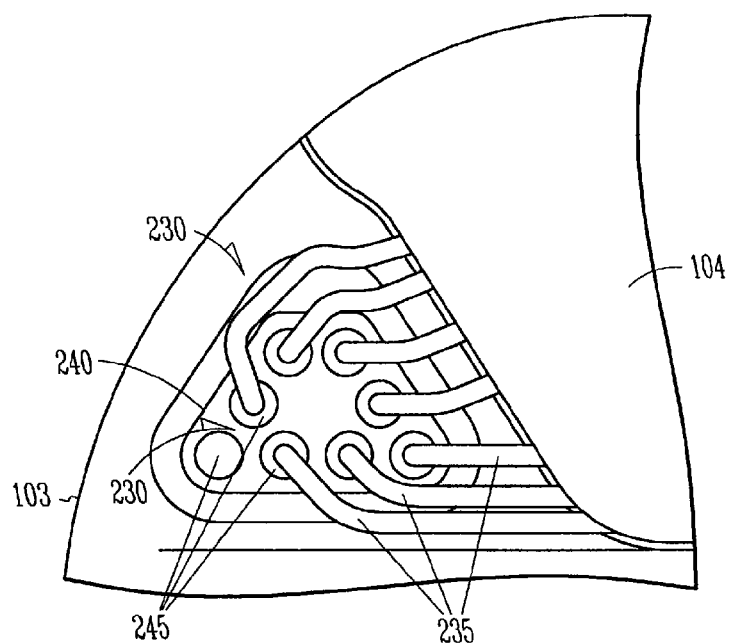
FIG. 3 shows a close up view of a connection between a header and a pulse generator housing, in accordance with one embodiment.

FIG. 2 illustrates a side exploded view of pulse generator housing 103 and header 104. FIG. 3 shows a close up view of a connection between header 104 and a pulse generator housing 103, in accordance with one embodiment.

Header 104 includes one or more longitudinal bores 140 that are configured to receive a lead terminal of lead 110 (FIG. 1). The lead terminal can include one or more contacts to contact corresponding contacts 220, 221 within header 104. In one embodiment, header 104 generally includes a header body 210 having the longitudinal bore 140 formed therein and the one or more electrical contacts 220, 221 located within the bore 140 to contact corresponding contacts of lead 110. Contacts 220, 221 are electrically connected to the electronics in pulse generator housing 103 via a grouping 230 of connectors 235. For example, each individual connector 235 is electrically coupled to one or more of contacts 220, 221. Each connector 235 is also connected to a feedthrough pin 245 of a feedthrough assembly 240 mounted to pulse generator housing 103. In turn, feedthrough pins 245 are electrically connected to electronic components with housing 103. In one embodiment, feedthrough pins 245 are oriented so as to define a connection surface generally parallel to a major surface 255 of the housing 103. In other words, feedthrough pins 245 are oriented so that each pin's longitudinal axis is perpendicular to surface 255.

Figure 4:
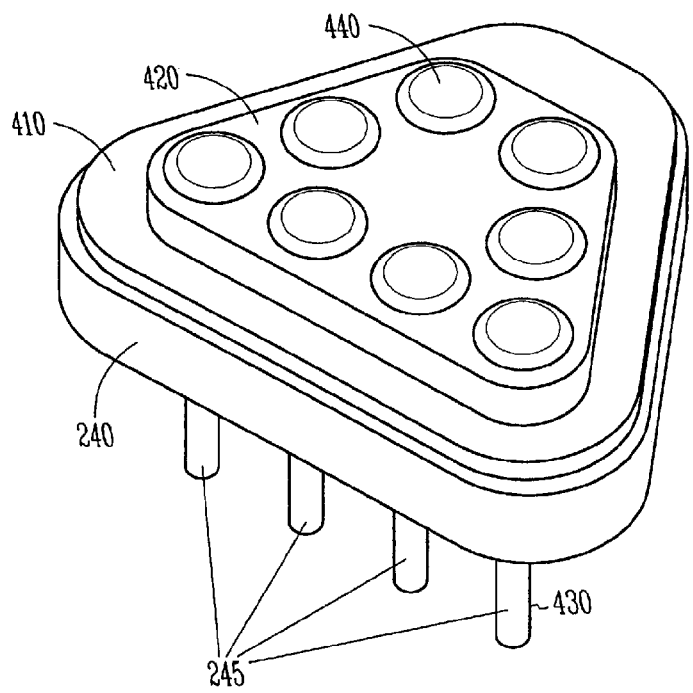
FIG. 4 shows a perspective view of a feedthrough assembly, in accordance with one embodiment.
Figure 5:
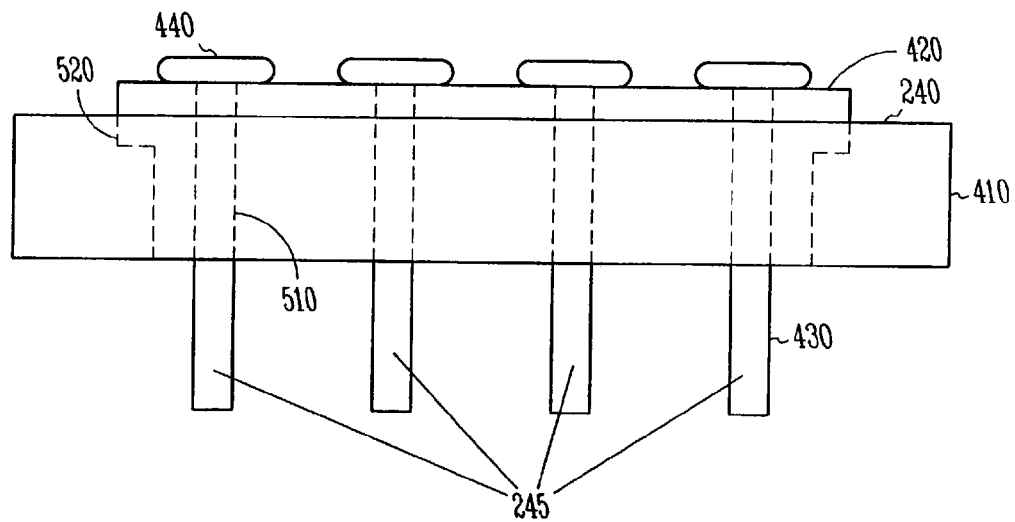
FIG. 5 shows a side view of the feedthrough assembly of FIG. 4.
Figure 6:
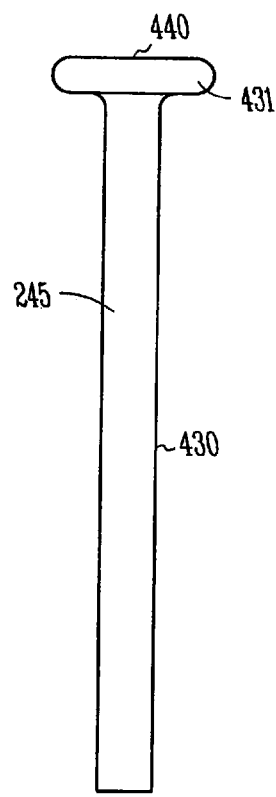
FIG. 6 shows a side view of a feedthrough pin, in accordance with one embodiment.

Referring now also to FIGS. 4, 5, and 6, FIG. 4 shows a perspective view of feedthrough assembly 240, FIG. 5 shows a side view of the feedthrough assembly, and FIG. 6 shows a side view of feedthrough pin 245, in accordance with one embodiment. Feedthrough assembly 240 includes a conductive portion 410, a nonconductive support base 420 and one or more feedthrough pins 245. Conductive portion 410 supports and is located around the periphery of nonconductive base 420. In one example, conductive portion 410 includes titanium and is laser welded to housing 103. Conductive portion 410 can further include a ledge 520 which supports part of nonconductive base 420. In one embodiment, base 420 can be attached to conductive portion 410 by a gold braze joint.

Non-conductive base 420 can include a ceramic, for example. Nonconductive base 420 includes one or more holes 510 therethrough. Holes 510 extend through the base 420 and are sized to receive feedthrough pins 245. In one example, feedthrough pins 245 are attached at holes 510 by brazing. Feedthrough assembly 240 further includes the one or more feedthrough pins 245, with each feedthrough pin 245 extending through one of the plurality of holes 510.

Each feedthrough pin 245 is a conductive material, such as Pt—Ir, and includes a shaft or other pin body 430 and a head 431 having an upper contact surface 440 for connecting to one or more of the electrical connectors 235 (FIG. 3). Upper contact surface 440 of each pin 245 has a larger surface area than a cross-sectional area of the pin body 430. In certain example, feedthrough pins 245 define a nailhead shape. As will be discussed, this provides more surface area for making the connection between connector 235 and feedthrough pin 245. A lower surface of head 431 is seated against the nonconductive base 420.

Referring again to FIGS. 2 and 3, in one embodiment, electrical connectors 235 extend from the header 104 and are positioned in a predetermined configuration such that the connectors retain their position as the header sub-assembly is mounted to the housing 103. For example, the connectors 235 can be wire ribbons that hold their shape as a group as originally configured. The sub-assembly of the header 104 can be assembled and then positioned on top of the housing 103. The feedthrough pins 245 are positioned in a configuration to substantially match the configuration of the one or more electrical connectors 235, such that the final location of the connectors 235 is such that they rest somewhere on or above the upper surface of feedthrough pins 245. This allows for ease of assembly since each separate connector 235 does not need to be individually routed from the header to a feedthrough pin. In contrast, in the present system each connector 235 is in the proper position as placed. Moreover, since the feedthrough pins 245 have expanded nailhead connection surfaces 440, there can be increased variation allowable between the locations of the connectors 235 relative to the feedthrough pins 245 and the connection can still be made successfully.

In one example, electrical connectors 235 include wire ribbons that are pre-formed in a curved or bent configuration so that at least a portion of each connector 235 is located on or above the upper contact surface 440 of feedthrough pin 245 when the header 104 is placed onto the housing 103. In other examples, electrical connectors 235 can include round wire connectors or combinations of round wires and/or ribbon connectors. The connectors 235 can be attached to the feedthrough pins 245 by welding, brazing, conductive epoxy or other techniques.

To assemble an implantable device 100 in accordance with one embodiment, header 104 sub-assembly is formed such that connectors 235 extend from the header 104 in a predetermined configuration. The header 104 is positioned over the housing 103 so that the connectors 235 are above or contact the upper surfaces 440 of feedthrough pins 245. If the connectors 235 are above the surface 440, then they are pressed down before connecting. The connectors 235 are then electrically and mechanically attached to the feedthrough pins 245 by welding, soldering, brazing, or conductive epoxy, for example. As noted, this eliminates the need for manually routing each individual connector from the header to the feedthrough to perform a connection. Moreover, since the pins 245 have a low profile relative to an upper surface of the support base 420 (See FIG. 5), the flat head connection surface 440 saves expensive material since the feedthrough pin 245 can be relatively shorter than a feedthrough that extends above the surface for attaching to a connector from a header. Also, this lower profile also allows for a slimmer housing 104 and overall pulse generator device 100. Also, as noted, the flat head broad surface connection 440 allows more variance in the precise location of connectors 235 from the header, which lowers manufacturing complexity.

Figure 7:
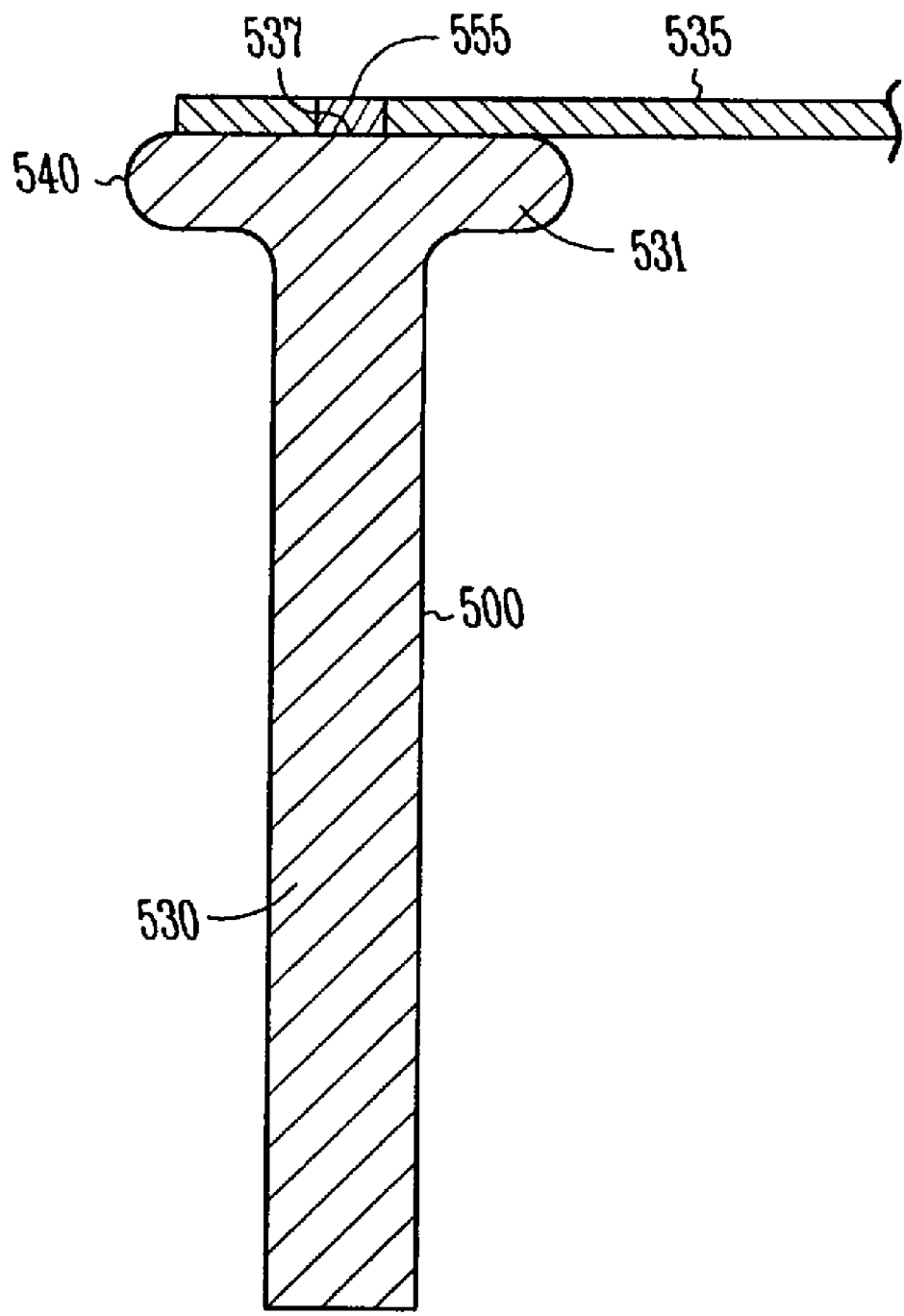
FIG. 7 shows a cross-section side view of a feedthrough pin, in accordance with one embodiment.

FIG. 7 shows a cross-section side view of a feedthrough pin 500, in accordance with one embodiment. In this example, feedthrough pin 500 is a conductive material, such as Pt—Ir, and includes a shaft or other pin body 530 and a head 531 having an upper contact surface 540 for connecting to one or more electrical connectors 535, which extend from a header, for example. Upper contact surface 540 of each pin 500 has a larger surface area than a cross-sectional area of the pin body 530. In this embodiment, pin 500 includes a protrusion 555 extending above surface 540. Connector 535 includes a corresponding hole 537. When assembling the connector 535 to the feedthrough pin 500, the user can press the connector 535 over the protrusion 555 so that the protrusion extends through hole 537. This helps align the connector relative to the feedthrough pin.

In other examples, the header discussed herein can include an antennae and/or electronic components that are used to electrically communicate outside the device.

It is understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. An implantable device comprising:
   a header;
   a housing;
   one or more electrical connectors connected to the header and located externally relative to the housing; and
   a feedthrough assembly mounted to the housing, the feedthrough assembly including a nonconductive base having one or more holes therethrough, the feedthrough assembly further including one or more feedthrough pins, each feedthrough pin extending through one of the one or more holes, each feedthrough pin including an integral structure including a pin body and an upper contact surface, wherein the upper contact surface is located externally of the housing for connecting to one or more of the electrical connectors, wherein the one or more feedthrough pins includes a nailhead shape with the upper contact surface having a larger connection surface area than a cross-sectional area of the pin body, wherein the pin body includes a lower pin body portion located internally and having a same diameter as a diameter as the rest of the pin body and smaller cross-sectional area than the upper contact surface.

2. The implantable device of claim 1, wherein the one or more electrical connectors are positioned in a predetermined configuration.

3. The implantable device of claim 2, wherein the one or more feedthrough pins are positioned in a configuration to substantially match the configuration of the one or more electrical connectors.

4. The implantable device of claim 1, wherein the nailhead shape portion of the at least one feedthrough pin is positioned above the nonconductive base.

5. The implantable device of claim 1, wherein the feedthrough assembly further includes a conductive portion mounted around the nonconductive base, the conductive portion attached to the housing.

6. The implantable device of claim 1, wherein at least one of the electrical connectors includes a ribbon connector.

7. The implantable device of claim 6, wherein the ribbon connector extends from the header and is pre-formed such that the ribbon connector is located at the upper contact surface of the feedthrough pin.

8. The implantable device of claim 1, wherein at least one of the electrical connectors is connected to the upper contact surface of one of the feedthrough pins.

9. The implantable device of claim 8, wherein the at least one electrical connector is connected to the upper contact surface of the one of the feedthrough pins by welding, brazing, soldering, or conductive epoxy.

10. The implantable device of claim 8, comprising a solder joint between the at least one of the electrical connectors and the upper contact surface of the one of the feedthrough pins.

11. The implantable device of claim 1, wherein one of the feedthrough pins includes a head and a shaft, and wherein a lower portion of the head is seated against the nonconductive base, and wherein an upper portion of the head is connected to at least one of the electrical conductors connected to the header.

12. An implantable device comprising:
a header;
a housing;
one or more electrical connectors connected to the header and located external relative to the housing, the one or more electrical connectors positioned in a predetermined configuration; and
a feedthrough assembly mounted to the housing, the feedthrough assembly including a plurality of feedthrough pins, each feedthrough pin including an integral structure including a pin body and an upper contact surface, wherein the upper contact surface is located external of the housing for connecting to one or more of the electrical connectors, wherein the one or more feedthrough pins includes a nailhead shape with the upper contact surface having a larger connection surface area than a cross-sectional area of the pin body, wherein the plurality of feedthrough pins are positioned in a configuration to substantially match the configuration of the one or more electrical connectors, and wherein the pin body includes a lower pin body portion located internally and having a same diameter as a diameter as the rest of the pin body and smaller cross-sectional area than the upper contact surface.

13. The implantable device of claim 12, wherein the nailhead shape portion of each of the feedthrough pins is positioned above the nonconductive base.

14. The implantable device of claim 12, wherein the feedthrough assembly further includes a conductive portion mounted around the nonconductive base, the conductive portion attached to the pulse generator housing.

15. The implantable device of claim 12, wherein at least one of the electrical connectors includes a ribbon connector.

16. The implantable device of claim 15, wherein the ribbon connector extends from the header and is preformed such that at least a portion of the connector is at or above the upper contact surface of the feedthrough pin.

17. A method comprising:
assembling a header subassembly for an implantable device such that a plurality of connectors extend from the header in a predetermined configuration;
placing the header subassembly onto a housing such that the connectors are on or above upper surfaces of feedthrough pins attached to the housing, wherein each of the feedthrough pins includes an integral structure including a pin body and an upper contact surface, wherein the upper contact surface is located external of the housing and wherein the upper contact surfaces of the feedthrough pins including a nailhead shape having a larger connection surface area than a cross-sectional area of the pin body, and wherein the pin body includes a lower pin body portion located internally and having a same diameter as a diameter as the rest of the pin body and smaller cross-sectional area than the upper contact surface; and
connecting the connectors to the feedthrough pins.

18. The method of claim 17, further comprising pressing down on the connectors before connecting the connectors to the feedthrough pins.

19. The method of claim 17, wherein connecting includes welding, soldering, or brazing.

20. The method of claim 17, wherein the feedthrough pins are oriented such that the upper surfaces of the feedthrough pins lie in a parallel plane to a major surface of the pulse generator housing.

* * * * *